United States Patent [19]
Bailey et al.

[11] Patent Number: 5,103,854
[45] Date of Patent: Apr. 14, 1992

[54] LOW PRESSURE CHECK VALVE FOR ARTIFICIAL RESPIRATION DEVICES

[75] Inventors: James C. Bailey, Yellow Springs; Dennis A. Boehmer, Xenia; Gordon E. Atkinson, Cedarville, all of Ohio

[73] Assignee: Vernay Laboratories, Inc., Yellow Springs, Ohio

[21] Appl. No.: 764,121

[22] Filed: Sep. 24, 1991

Related U.S. Application Data

[63] Continuation of Ser. No. 599,316, Oct. 17, 1990, abandoned, which is a continuation-in-part of Ser. No. 468,424, Jan. 22, 1990, Pat. No. 4,986,310.

[51] Int. Cl.⁵ .............................................. F16K 11/10
[52] U.S. Cl. .............................. 137/102; 128/205.24; 137/512.2; 137/512.4
[58] Field of Search ................... 137/102, 512.2, 512.4; 128/205.24

[56] References Cited

U.S. PATENT DOCUMENTS

| | | |
|---|---|---|
| 2,758,609 | 8/1956 | Dickert et al. |
| 3,085,591 | 4/1963 | Schneider |
| 3,435,839 | 4/1969 | Elder ................................ 137/102 |
| 3,739,801 | 6/1973 | Rudolph ............................ 137/102 |
| 3,741,232 | 6/1973 | Soberski ............................ 137/102 |
| 4,188,978 | 2/1980 | De Lorenzo ...................... 137/859 |
| 4,712,583 | 12/1987 | Pelmulder et al. ............... 137/852 |

Primary Examiner—Robert G. Nilson
Attorney, Agent, or Firm—Biebel & French

[57] ABSTRACT

A valve assembly is disclosed for controlling fluid flow in a first direction and a second direction. The valve assembly includes a housing for enclosing a substantially circular regulator assembly which extends diametrically across the housing. The regulator assembly comprises a hub portion which is positioned centrally within the housing and connecting members which extend radially toward a rim portion which is supported by the housing. The hub portion supports a disk-shaped substantially inflexible portion of the regulator assembly which extends over the connecting members to engage the rim portion and thereby prevent fluid flow in a reverse flow direction through the regulator assembly. The connecting members of the regulator assembly are adapted to flex and allow the disk portion to move off of the rim and thereby allow fluid flow through the valve in the first direction.

16 Claims, 4 Drawing Sheets

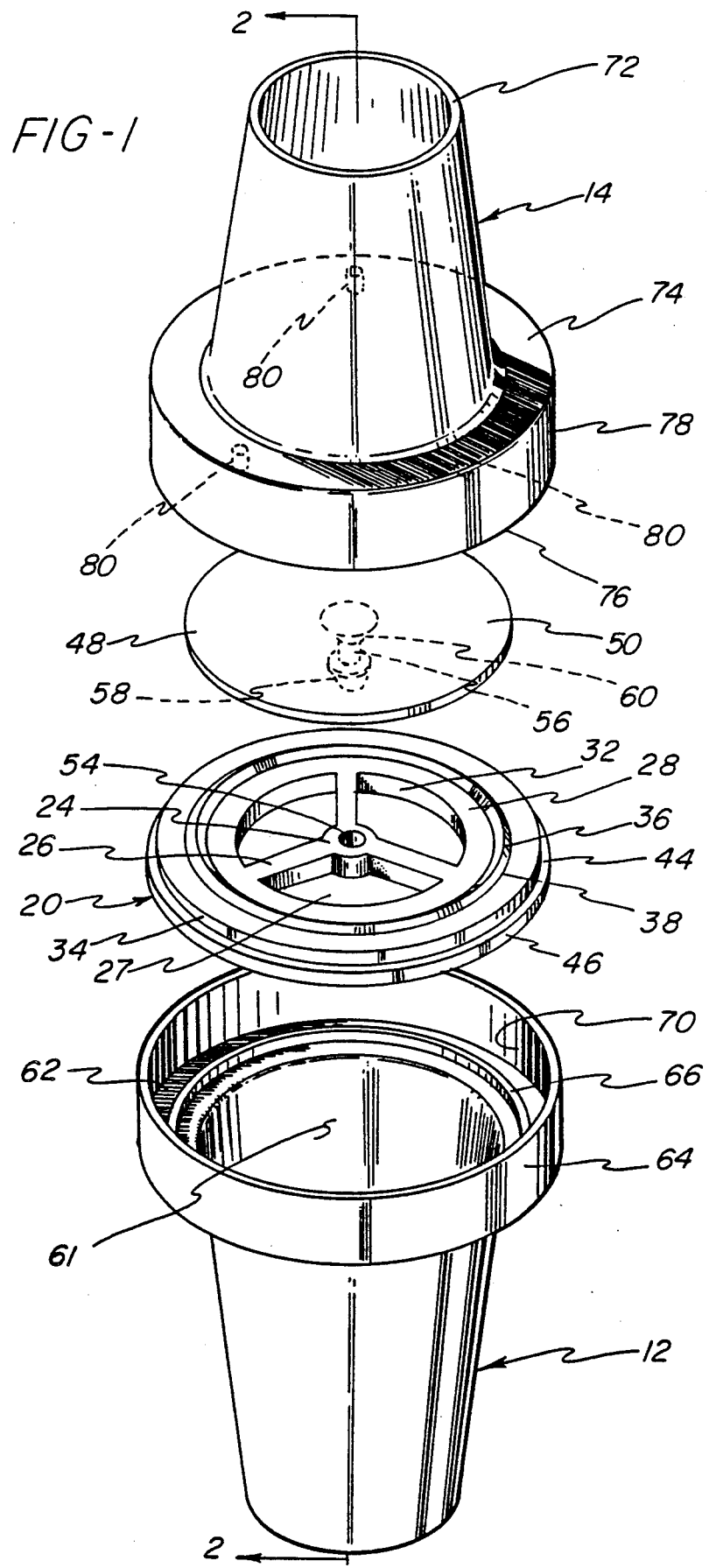

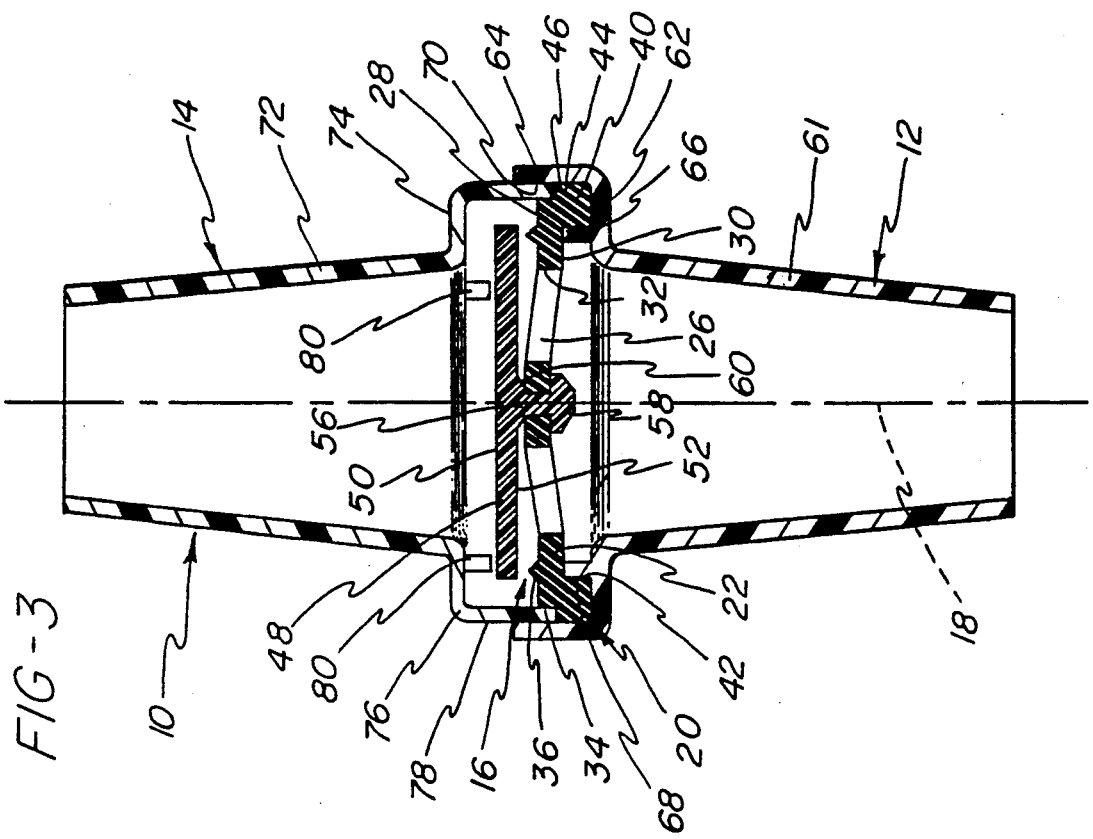
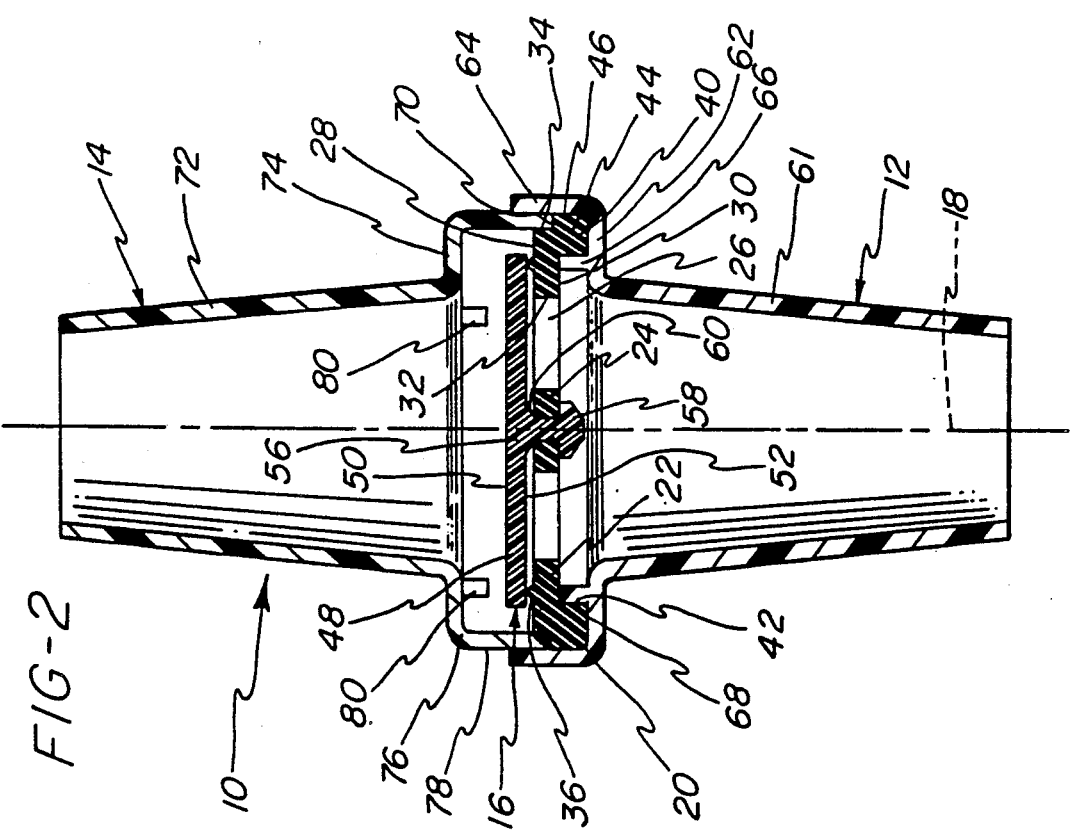

LOW PRESSURE CHECK VALVE FOR ARTIFICIAL RESPIRATION DEVICES

CROSS-REFERENCE TO RELATED APPLICATIONS

This application is a continuation of Ser. No. 599,316, filed Oct. 17, 1990, now abandoned, which is a continuation-in-part of application Ser. No. 468,424, filed Jan. 22, 1990, now U.S. Pat. No. 4,986,310.

BACKGROUND OF THE INVENTION

The present invention relates generally to a flow regulation apparatus, and more particularly, to a one-way check valve which will open at very low pressures to allow high flow rates in a first direction and which will close to prevent flow in a second direction.

One requirement of one-way flow valves, such as the type used as check valves in positive crankcase ventilation systems for internal combustion engines, is that the valves must offer little resistance to fluid flow in one direction but will completely stop fluid flow in the opposite direction. A valve which is commonly used for this purpose is a poppet valve which comprises an axially movable valve member which is typically biased toward a valve seat by a helical spring. This type of valve suffers from the problem of requiring numerous structural elements to maintain the alignment of the movable valve member and to provide the biasing force to close the valve. In addition, the weight of the movable valve member results in this member having too much inertia to respond quickly to sudden changes in direction of the fluid flow at low pressures.

Another valve which is known in the art for limiting flow in one direction and providing a high flow rate is the umbrella valve. In the umbrella valve, the movable valve member is formed of a flexible material and has a generally curved cross-section. Hoop stresses in the radially outer portions of the valve member produce the spring force biasing the valve closed which must be overcome to open the valve. Thus, umbrella valves are designed to initially open at a small predetermined pressure and subsequently open further to provide a large flow rate with an increase in pressure.

In other applications, such as valves used in artificial respiration devices, a duckbill check valve may be used in combination with a diaphragm member to forcibly convey air to a patient from an air bag, while preventing exhaled air from being returned to the bag. In such an application, the valve must also be capable of preventing back flow of fluids such as vomit. Known respirator valves typically produce too much resistance to the flow from the bag to the patient, which in turn creates excessive back pressure within the bag such that attending personnel applying squeezing force to the bag will tire quickly. In addition, respiration devices incorporating duckbill valves often produce an objectionable honking noise.

While known check valves are satisfactory for many applications, the ability of known valves to respond at low pressures typically decreases as the size of the valve and the volume of fluid flow conducted by the valve is increased. Thus, there exists a need for a valve which is capable of permitting high fluid flow rates at very low pressures. In addition, there exists a need for a valve which will open and close quickly in response to changes in direction of the fluid flow and which will not collapse when subjected to high pressures in a reverse flow condition.

Further, there is a need for a valve which is capable of quiet operation while providing high flow rates at very low pressures and which may be incorporated into conventional structure for artificial respiration devices.

SUMMARY OF THE INVENTION

The present invention is a valve assembly for allowing high fluid flow rates at a low pressure in a first direction and for preventing fluid flow at high pressures in a second opposite direction.

The valve assembly comprises a housing which may have a tubular shape having inlet and outlet portions. The inlet and outlet portions are adapted to telescopingly fit within each other for enclosing a flow regulator assembly within the housing.

The flow regulator assembly includes a flexible elastic element having a rim portion, a hub portion, and connecting members extending from the hub portion to the rim portion such that the rim, hub and connecting members define apertures through the elastic element.

The rim of the elastic element includes a raised bead portion on one surface thereof on the outlet side of the valve assembly. The outer edge of the rim is rigidly supported by the housing. A thin disk made of an inelastic relatively inflexible material such as plastic is supported by the hub portion of the elastic element and has a diameter which is slightly greater than the diameter defined by the raised bead portion on the rim of the elastic element. In addition, the housing includes a raised lip portion located on the inlet side of the elastic element such that when a pressure is applied from the outlet portion toward the inlet portion of the housing, the disk, which normally rests upon the bead portion at the outlet side of the elastic element, will be forced firmly onto the bead portion and the raised lip will support the elastic element and prevent it from moving.

When a fluid flow occurs from the inlet to the outlet side of the housing, the disk is lifted away from the bead portion of the elastic element, thereby flexing the connecting members such that the fluid flows through the apertures in the elastic element and around the edges of the disk to pass out through the outlet portion of the housing.

In an alternative embodiment, the raised bead portion may be located on the disk for engaging an opposing surface on the rim of the elastic element and thereby forming a seal for preventing fluid flow as described above.

Thus, the valve of the present invention provides a light movable disk element which presents a large surface area to pressure differentials occurring on opposite sides of the valve, such that small pressure differentials within the valve result in quick opening and closing movements of the disk.

In addition, the connecting members supporting the disk provide a flexible support means for the disk while presenting a minimum restriction to the flow through the elastic element such that large fluid flows may be obtained when the valve is open.

In another embodiment of the invention, the abovedescribed flow regulator assembly is incorporated into the diaphragm structure of an artificial respiration device. In this embodiment of the invention, the regulator assembly is provided for preventing back flow of gases to an air supply bag, while also being movable with the diaphragm to permit exhaled gases to escape through vent holes in the housing of the artificial respiration device.

Other objects and advantages of the invention will be apparent from the following description, the accompanying drawings and the appended claims.

DESCRIPTION OF THE DRAWINGS

FIG. 1 is a perspective exploded view of a preferred embodiment of the one-way check valve of the present invention;

FIG. 2 is an elevational view of a cross-section along line 2—2 in FIG. 1;

FIG. 3 is an elevational view similar to FIG. 2 in which the valve is shown open for moderate flow;

DESCRIPTION OF THE PREFERRED EMBODIMENT

Figure 4:
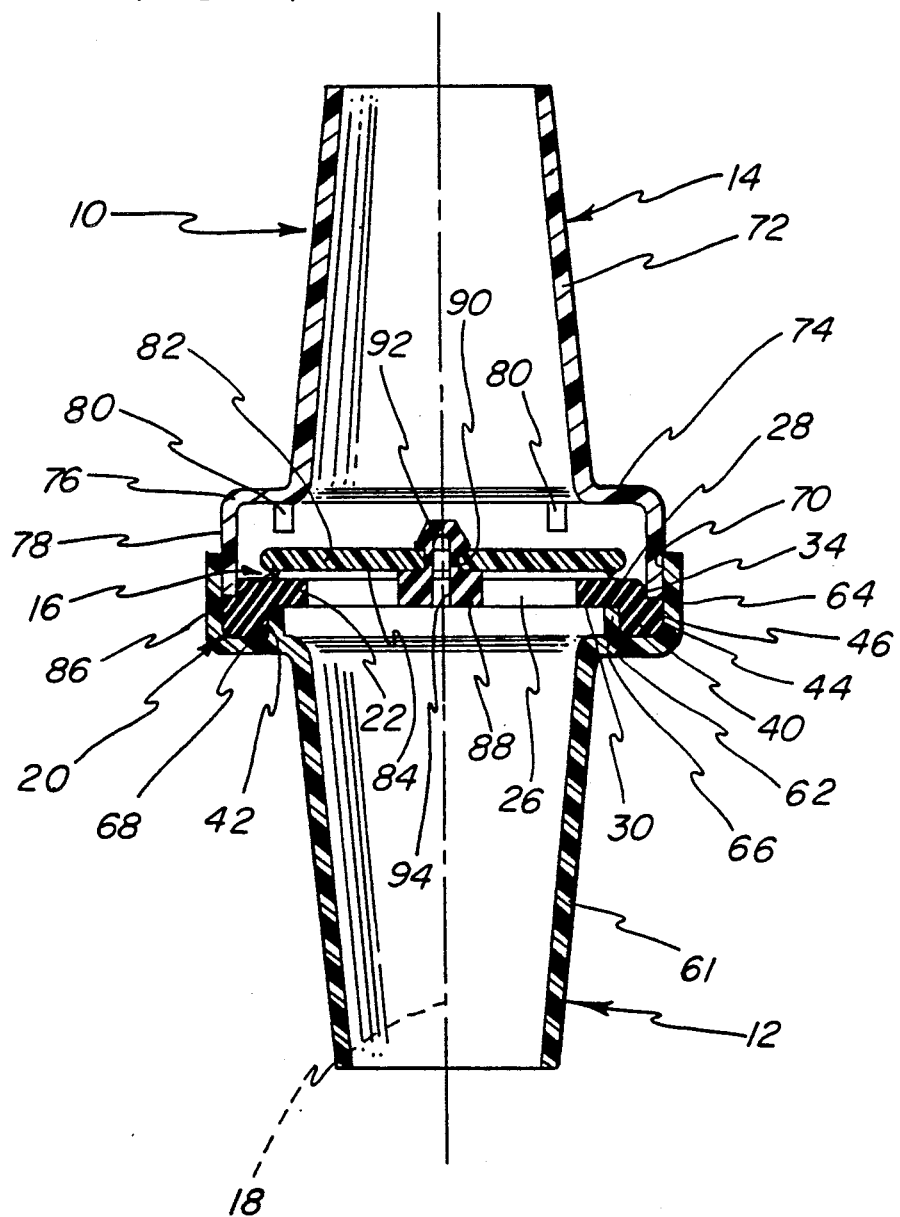
FIG. 4 is an elevational view similar to FIG. 2 showing an alternative embodiment of the present invention.

The valve assembly of the present invention, generally designated 10, includes a housing formed of an inlet portion 12 and an outlet portion 14. The inlet and outlet portions 12, 14 may be formed as tubular members and are joined together to house a substantially circular regulator assembly 16. The inlet portion 12, outlet portion 14 and regulator assembly 16 are formed as substantially symmetrical elements about the longitudinal axis 18.

Referring to FIGS. 1-3, the regulator assembly 16 includes a flexible element 20 formed of an elastic material and is preferably formed of an elastomeric material such as rubber. The flexible element 20 has a substantially circular rim portion 22, a hub portion 24, and connecting members 26 extending radially from the hub portion 24 to the rim portion 22. The rim, hub and connecting members 22, 24, 26 define apertures 27 in the flexible element 20 for passage of fluids therethrough. The rim portion 22 is formed with a first substantially planar side 28 facing toward the outlet portion 14 and an opposing second substantially planar side 30 and radially spaced inner and outer surfaces 32 and 34, respectively.

The rim 22 further includes a bead portion 36 which extends axially from the first side 28. The bead portion 36 is a continuous substantially circular raised element and is positioned between the inner and outer surfaces 32, 34 and defines an outer diameter 38 where the bead 36 joins the rim 22 at a point on the bead 36 which is radially distal from the hub 24.

A substantially circular foot portion 40 extends axially from the second side 30 of the rim 22 and is located adjacent to the outer surface 34 thereof. The foot portion 40 includes an inner wall 42 which defines an inner diameter thereof where the foot portion 40 joins the rim portion 22. The inner diameter of the foot portion is substantially equal to the outer diameter 38 of the bead portion 36. The foot portion 40 further includes a flange portion 44 which extends radially beyond the outer surface 34 of the rim 22 to define an outer foot surface 46.

The regulator assembly 16 further includes a substantially circular relatively inflexible or rigid disk 48 which is preferably formed of a thin lightweight and inelastic material such as plastic. The disk 48 includes first and second substantially planar surfaces 50 and 52 and has a diameter slightly greater than the outer diameter 38 of the bead portion 36 such that the second surface 52 may engage the bead portion 36 in spaced relation to the first surface 28 of the rim 22 and thereby form a seal between the disk 48 and the flexible element 20.

The hub 24 of the flexible element 20 includes means defining a hole 54 therethrough for receiving a rod member 56 which projects from the second surface 52 of the disk 48 and which is located substantially centrally on the disk 48. The rod member 56 includes a generally conically shaped enlarged portion 58 which is formed with a diameter larger than that of the rod member 56 and the hole 54 such that the member 58 acts to hold the rod 56 in place within the hub 24. In addition, a substantially circular ramp portion 60 surrounds the rod 56 adjacent to the disk 48 and extends from the hole 54 in the hub 24 to the second surface 52 of the disk 48. The height of the ramp 60 in the axial direction is preferably equal to the height of the bead portion 36 and acts to space the hub 24 from contacting the second surface 52 of the disk 48.

The inlet portion 12 of the housing includes a side wall 61 and a flange 62 which extends radially outwardly from the wall 61. A first substantially circular lip 64 extends axially from a radially outer edge of the flange 62 and a second substantially circular lip 66 extends axially from the flange 62 at a location between the wall 61 and the first lip 64. The second lip 66 extends from the flange 62 a lesser distance than the first lip 64 and a radially outer surface 68 of the second lip 66 defines an outer diameter which is substantially equal to the inner diameter defined by the surface 42 of the foot portion 40. In addition, the first lip 64 includes an inner surface 70 which defines an inner diameter substantially equal to the diameter defined by the outer surface 46 of the foot 40 such that a groove is formed between the first and second lips 64, 66 for receiving the foot portion 40 of the flexible element 20 and wherein the second lip 66 acts as a support for the second surface 30 of the rim portion 22.

The outlet portion 14 of the housing includes a wall 72 and a flange 74 which extends radially outwardly from the wall 72. A substantially circular lip 76 extends axially from a radially outer edge of the flange 74 and includes an outer wall 78 which defines a diameter which is slightly smaller than the diameter defined by the wall 70 of the lip 64 such that the lip 76 of the outlet portion 14 may be received in telescoping relation within the first lip 64 of the inlet portion 12.

One or more stop members 80 in the form of rod-shaped projections extend from the flange 74 of the outlet portion 14 at a location between the wall 72 and the lip 76 and are located on a diameter which is smaller than that of the disk 48. The stops 80 are equally spaced from one another and extend from the flange 74 a lesser distance than that of the lip 76. Alternatively, a single stop may be located centrally of the outlet portion 14 and supported by thin supporting members extending radially inwardly from the wall 72, such that the single stop is directed toward the disk 48.

The lip 76 of the outlet portion 14 engages the flange 44 of the foot portion 40 such that the foot portion 40 is held in position between the outlet portion lip 76 and the inlet portion flange 62, thereby forming a seal between the rim and the housing.

In operation, as may be best seen in FIGS. 2 and 3, the disk 48 and hub 24 form a lightweight unit supported for movement by the connecting members 26 wherein the disk 48 is normally in engagement with the bead portion 36 of the flexible element 20 to form a seal therebetween. In addition, when a greater fluid pressure is applied through the outlet portion 14 than through the inlet portion 12, the disk 48 is further forced into engagement with the bead 36 such that a strong seal preventing fluid flow is formed between the disk and bead portions.

When a greater fluid pressure is applied through the inlet portion 12 than through the outlet portion 14, the fluid forces the disk 48 to move toward the outlet portion 14 and out of engagement with the bead portion 36 along a line substantially parallel to the longitudinal axis 18 such that the fluid may flow through the apertures 27 between the connecting members 26 and around the outer edge of the disk 48 and then through the passage defined by the tubular wall 72.

As may be seen in FIG. 3, the flexible element 20 deflects primarily at the connecting members 26 when the disk 48 and the hub 24 to which it is connected are forced toward the outlet portion 14. As the disk 48 is moved toward the outlet portion 14, it approaches the stops 80 which act to space the disk 48 from the flange 74 to positively limit the movement of the disk 48 and thereby prevent damage to the flexible element 20 resulting from overstretching the connecting members 26, as well as ensure that fluid flow will continue around the edges of the disk 48 and the upper surface 50 thereof.

It should be apparent that by using a disk as the actuating member for the valve of the present invention, a large surface area is presented to pressure differentials occurring on opposite sides of the valve, such that the disk is capable of being actuated by very low forward flow pressures.

In addition, it should be apparent that as a result of the disk 48 seating on the bead 36 at the outer supported edge of the flexible element 20, such that check pressures are transmitted from the disk 48 to the supporting lip 66 along a line which is substantially parallel to the longitudinal axis 18, a positive seal is provided while enabling the regulator assembly to withstand extremely high check pressures without danger of the valve elements collapsing and thereby allowing reverse fluid flows through the valve.

Further, by constructing the disk 48 as a thin member formed of a lightweight material, the weight of the moving element of the valve is kept to a minimum, thereby ensuring that the valve may be actuated quickly upon changes in direction of the fluid flow and that the valve will function properly regardless of the orientation of the valve assembly.

In a practical application of the valve, such as within a positive crank case ventilation system for an internal combustion engine, the regulator assembly portion of the valve may be constructed having approximately an inch diameter and the stops may be positioned such that the disk undergoes a movement of approximately 40 thousandths of an inch to open the valve. The pressure at which the valve will open may be controlled by altering the height of the bead portion 36 or alternatively, changing the length of the rod member 56 to vary the amount of preload present for biasing the disk 48 into contact with the bead portion 36.

It should be noted that other embodiments of this valve may be formed which function in the same manner as the above-described valve structure. FIG. 4 shows an alternative embodiment in which the elements which are unchanged from the previous embodiment are identified with the same reference numerals as that embodiment.

In the embodiment shown in FIG. 4, a disk 82 similar to the disk 48 of the previous embodiment is provided and includes a lower surface 84 having a substantially circular raised bead 86 extending therefrom toward the surface 28 of the rim 22 which is now formed without a bead. The bead 86 of the present embodiment is formed with substantially the same diameter as the bead 36 of the previous embodiment.

In addition, the flexible element 20 is provided with a hub 88 which extends beyond the plane of the surface 28 a distance approximately equal to the axial height of the bead 86 on the disk 82. An elongated extension 90 extends axially from the hub 88 and terminates in a generally conically-shaped enlarged end 92. The extension 90 extends through a hole in the disk 82 and the enlarged end 92 and hub 88 cooperate with opposing surfaces of the disk 82 to hold the disk 82 in place on the flexible element 20.

The hub 88 and extension include a hole 94 extending therethrough in a longitudinal direction. The hole 94 further lightens the movable portion of the valve as well as facilitates compression of the extension 90 and enlarged end 92 for insertion into the disk 82.

Further, other methods of attaching the disk and the flexible element together have been contemplated. For example, these elements may be held together by means of a pop-rivet or other fastener means. Although such attachment means may add to the weight of the movable member, they may be satisfactory for certain applications of the valve.

Figure 5:
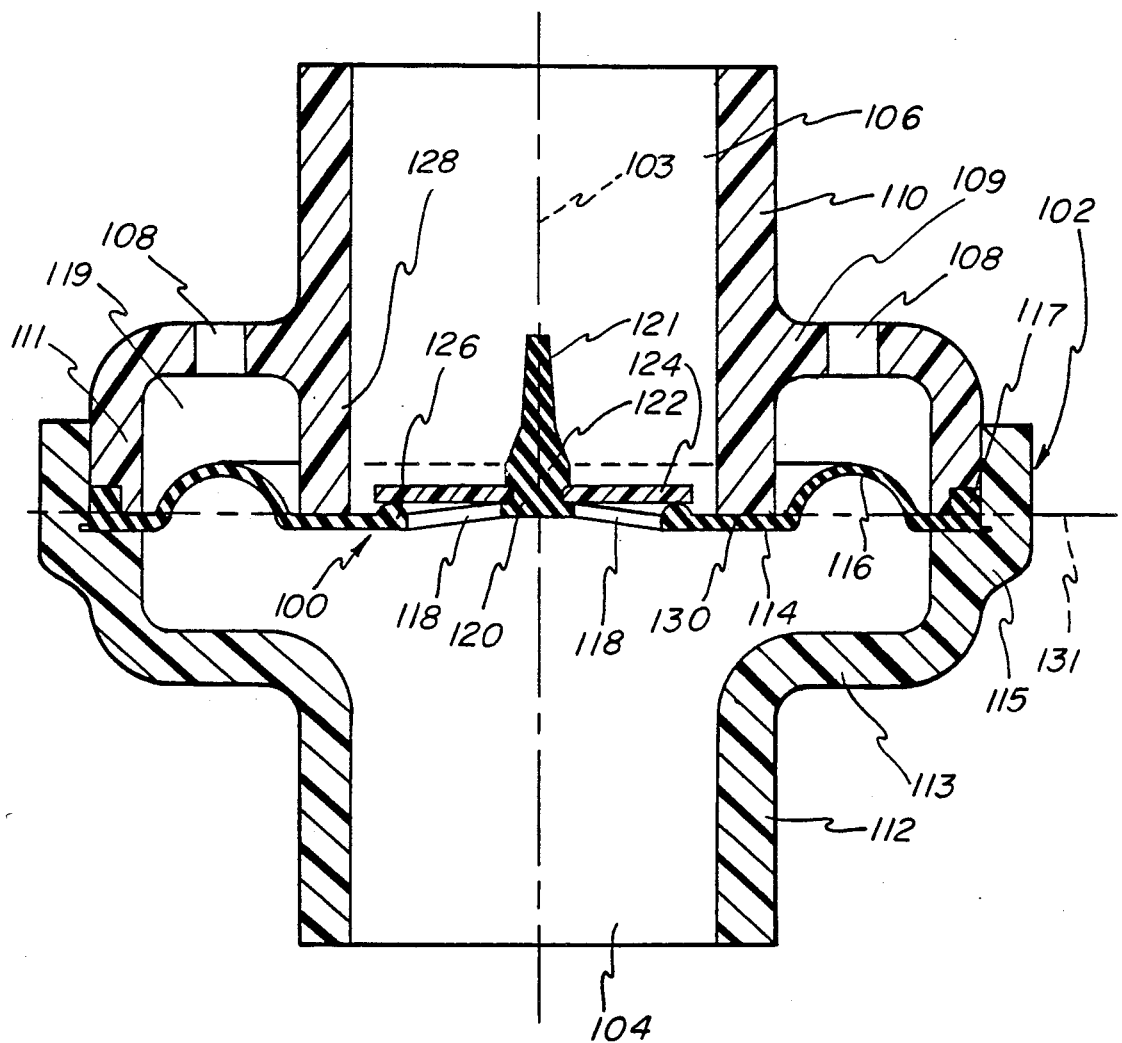
FIG. 5 is an elevational view in cross-section of an alternative embodiment in which the one-way check valve is incorporated into an artificial respiration device.

Referring to FIG. 5, the elements forming the regulator assembly of the check valve are shown incorporated into an artificial respiration device. In this embodiment, a diaphragm assembly 100 is mounted within a housing 102 for an artificial respiration device, and the diaphragm assembly 100 and housing 102 are preferably formed symmetrically about a central axis 103.

The housing 102 includes a first opening 104 formed in a housing half 112 and a second opening 106 formed in another housing half 110. The housing half 110 includes a radially outwardly extending flange portion 109 and a lip portion 111 which extends substantially perpendicularly from the flange portion 109.

Similarly, the housing half 112 includes a radially extending flange portion 113 and a lip lip portion 115 which extends substantially perpendicularly from the flange portion 113. The lip portions 111, 115 mate with each other to hold the diaphragm assembly 100 in position within the housing 102.

The flange portion 109 of the housing half 110 includes means defining a plurality of vent passages or holes 108 which are disposed radially inwardly from the lip portion 111 and radially outwardly from the second opening 106.

The diaphragm assembly includes a diaphragm member 114 formed of an elastomeric material and extending around a peripheral interior portion of the housing 102. A flange portion 117 extending around an outer peripheral portion of the diaphragm member 114 provides means for positively positioning and holding the diaphragm assembly 100 in place between the two housing halves 110, 112. The diaphragm member 114 includes at least one convolution 116 which provides increased flexibility for movement of the diaphragm 114. As may be seen in FIG. 5, the flange portion 117 is located radially outwardly from the convolution 116, and the convolution 116 and flange portion 117 are substantially aligned with the axial position of the first and second regulator portions with respect to the central axis 103.

The diaphragm assembly 100 further includes a regulator assembly attached to the diaphragm member 114 and which is substantially similar to the valve structure of the previous embodiments. The regulator assembly includes a first regulator portion having connecting members 118 extending radially inwardly toward a hub portion 120 from a rim portion having a raised bead portion 126. The first regulator portion may be formed of the same material as the diaphragm member 114 and is preferably formed integrally with the diaphragm member 114. As in the previous embodiments, the connecting members 118, rim portion and hub portion 120 define a plurality of apertures in the first regulator portion through which fluid may flow.

The hub portion 120 includes an extension 121 having an enlarged portion 122 for holding a second regulator portion defined by a disk 124 in place on the hub 120 of the first regulator portion. As in the previous embodiments, the disk 124 may be formed of a relatively inflexible plastic and includes a lower surface which contacts and forms a seal with the bead portion 126 of the first regulator portion.

The housing 102 is further provided with a seal portion 128 extending from the first housing half 110 toward the diaphragm member 114 for contacting and forming a seal with the diaphragm member 114 along a contact surface 130. The seal portion 128 extends around the entire circumference of and is located radially outwardly of the regulator assembly, and is located radially inwardly from the convolution 116 of the diaphragm member 114.

As may be seen in FIG. 5, the contact surface 130 positions the diaphragm member 114 in a common plane 131 with the flange portion 117. Further, the plane 131 passes through the hub portion 120 of the regulator assembly below the enlarged portion 122 at substantially the same location as the point of intersection between the control axis 103 and the hub portion 120 below the enlarged portion 122.

It should also be noted that the seal portion 128, flange 109 and lip portion 111 define a chamber 119 extending around the periphery of the housing half 110, and the convolution 116 extends up into the chamber 119 when the contact surface 130 engages the diaphragm member 114.

In operation, a compressible air bag is attached in fluid communication with the first opening 104 of the valve housing 102 and the second opening 106 is placed in fluid communication with a patient's respiratory system. As the bag is compressed, air is forced from the first opening 104 toward the second opening 106 thus causing the disk 124 to move away from the bead portion 126 such that the air may flow freely to the patient. During the operation of conveying the air from the bag to the patient, the diaphragm member 114 remains in contact with the contact surface 130 of the seal portion 128 to thereby prevent air from flowing out of the housing 102 through the vent holes 108.

When pressure on the air bag is released, the patient exhales gases which force the disk 124 down onto the bead portion 126 of the first regulator portion to thereby prevent the exhaled gases from returning to the air bag. Further, the exhaled gases also cause the diaphragm assembly 100 to move toward the first opening 104 such that the diaphragm member 114 is moved out of sealing contact with the seal portion 128, and the exhaled gases are discharged out of the housing through the vent holes 108. It should be apparent that the convolution 116 facilitates the movement of the diaphragm assembly 100 during the passage of the gases from the second opening 106 through the vent holes 108.

By incorporating the valve of the present invention into an artificial respiration device, the resistance to air flow through the valve is minimized such that the effort required to squeeze the air supply bag is drastically reduced, thus enabling the attending personnel to operate the bag for an extended period of time without undue fatigue. In addition, the present valve provides an advantage over prior art valves in that it does not produce objectionable noises during operation. Further, the valve of the present invention acts as an effective barrier to gases and fluids expelled by the patient whereby contamination of the air supply bag is prevented.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A valve for controlling fluid flow in a first and a second direction comprising:
   a housing defining a central axis and having means defining first and second openings;
   a regulator assembly having a first flexible regulator portion and a second relatively inflexible regulator portion, said central axis intersecting said regulator assembly;
   said first regulator portion extending diametrically across said housing to separate said first opening from said second opening and having means defining apertures for allowing fluid flow in said first direction from said first to said second opening;
   said second regulator portion attached to said first regulator portion and including a sealing surface for contacting said first regulator portion for preventing fluid flow through said apertures in a direction from said second to said first opening;
   means for attaching said regulator assembly to said housing including a flexible diaphragm member extending between said first regulator portion and said housing, said diaphragm member having a convolution formed therein whereby movement of said regulator assembly relative to said housing is permitted while said second regulator portion is in sealing contact with said first regulator portion;
   said first regulator portion being adapted to flex whereby said second regulator portion is caused to move relative to said housing to allow said sealing surface of said second regulator portion to separate from said first regulator portion during fluid flow in said first direction;
   a seal portion extending from said housing toward said diaphragm, said seal portion including a contact surface for contacting and forming a seal with said first regulator portion at a location radially inwardly from said convolution and radially outwardly from said sealing surface on said second regulator portion; and a peripheral flange located radially outwardly from said convolution for mounting said diaphragm to said housing, wherein said convolution and said peripheral flange are substantially axially aligned with said first and second regulator portions such that a plane defined by said flange portion intersects said central axis at substantially the same longitudinal location along said central axis as a point of intersection of said regulator assembly with said central axis.

2. The valve of claim 1 including means in said housing defining vent holes from an exterior portion to an interior portion of said housing, said contact surface forming a seal with said diaphragm to prevent said fluid flow in said first direction from passing through said vent holes.

3. The valve of claim 2 wherein said fluid flow in said second direction causes said diaphragm to move away from said contact surface whereby fluid flow in said second direction passes from said second opening through said vent holes.

4. The valve of claim 1 including a chamber portion defined by said seal portion and said housing and extending around the periphery of said second opening.

5. The valve of claim 1 wherein said central axis passes through said first and second openings.

6. A valve for controlling fluid flow in a first and a second direction comprising:

a housing defining a central axis and having means defining first and second openings;

a regulator assembly having a first flexible regulator portion and a second relatively inflexible regulator portion, said central axis intersecting said regulator assembly;

said first regulator portion extending diametrically across said housing to separate said first opening from said second opening and having means defining apertures for allowing fluid flow in said first direction from said first to said second opening;

said second regulator portion attached to said first regulator portion and including a sealing surface for contacting said first regulator portion for preventing fluid flow through said apertures in a direction from said second to said first opening;

means for attaching said regulator assembly to said housing including a flexible diaphragm member extending from said first regulator portion to an attachment point on said housing, said diaphragm member permitting movement of said regulator assembly relative to said housing while said second regulator portion is in sealing contact with said first regulator portion;

said first regulator portion being adapted to flex whereby said second regulator portion is caused to move relative to said housing to allow said sealing surface of said second regulator portion to separate from said first regulator portion during fluid flow in said first direction;

said housing including means defining vent holes, wherein fluid flow in said second direction passes from said second opening through said vent holes;

a seal portion extending from said housing toward said diaphragm, said seal portion including a contact surface for contacting and forming a seal with said diaphragm at a location radially outwardly from said sealing surface on said second regulator portion to thereby prevent fluid flow through said vent holes during said fluid flow in said first direction; and a flange portion located on an outer peripheral edge of said diaphragm for mounting said diaphragm to said housing, wherein said flange portion is substantially axially aligned with said first and second regulator portions such that a plane defined by said flange portion intersects said central axis at substantially the same longitudinal location along said central axis as a point of intersection of said regulator assembly with said central axis.

7. The valve of claim 6 wherein said fluid flow in said second direction causes said diaphragm to separate from said contact surface.

8. The valve of claim 6 including a convolution formed in said diaphragm between said regulator assembly and said attachment point.

9. The valve of claim 6 including a chamber portion defined by said seal portion and said housing and extending around the periphery of said second opening.

10. The valve of claim 6 wherein said central axis passes through said first and second openings.

11. A valve for use in an artificial respiration device comprising:

a housing defining a central axis and including means defining first and second fluid passages and means defining a vent passage;

diaphragm means extending across said housing to separate said first and second fluid passages, said central axis intersecting said diaphragm means;

a seal portion extending from said housing to contact and form a seal with said diaphragm means whereby said second fluid passage may be maintained out of fluid contact with said vent passage;

said diaphragm means including aperture means extending through and defined by a flexible portion of said diaphragm, and a relatively inflexible movable member extending over said aperture means and contacting said diaphragm means to thereby prevent fluid flow through said aperture means in a direction from said second to said first fluid passage, said seal portion contacting said diaphragm radially outwardly from said aperture means;

a flange portion located on an outer peripheral edge of said diaphragm for mounting said diaphragm to said housing, wherein said flange portion is substantially axially aligned with said movable seal member and said aperture means such that a plane defined by said flange portion intersects said central axis at substantially the same longitudinal location along said central axis as a point of intersection of said diaphragm means with said central axis; and wherein a portion of said movable seal member may move out of contact with said diaphragm means when said seal portion is in contact with said diaphragm means to thereby permit fluid flow in a direction from said first to said second fluid passage.

12. The valve of claim 11 wherein said movable seal member is maintained in contact with said diaphragm means and said diaphragm means is moved out of contact with said seal portion when a fluid pressure is applied in the direction from said second to said first fluid passage whereby fluid is directed out of said housing through said vent passage.

13. The valve of claim 11 wherein said diaphragm means includes a centrally located flexible first regulator portion and said movable seal means is a second regulator portion attached to said first regulator portion, said first and second regulator portions being located radially inwardly from said seal portion.

14. The valve of claim 13 wherein said first regulator portion includes radially extending connecting members for supporting said second regulator portion, said connecting members being adapted to flex whereby said second regulator portion is caused to move relative to said housing.

15. The valve of claim 11 including a chamber portion defined by said seal portion and said housing and extending around the periphery of said second fluid passage.

16. The valve of claim 11 wherein said central axis passes through said first and second fluid passages.

* * * * *

UNITED STATES PATENT AND TRADEMARK OFFICE
CERTIFICATE OF CORRECTION

PATENT NO. : 5,103,854
DATED : April 14, 1992
INVENTOR(S) : James C. Bailey et al It is certified that error appears in the above-identified patent and that said Letters Patent is hereby corrected as shown below:

Column 9, line 4, after "convolution" --and engaging said housing-- has been omitted; line 46, "axially" should be deleted.

Column 10, line 5, after "diaphragm", first occurrence, --and engaging said housing-- has been omitted; line 7, "axially" should be deleted; line 46, after "diaphragm", first occurrence, --and engaging said housing-- has been omitted; line 48, "axially" should be deleted.

Signed and Sealed this

Twentieth Day of July, 1993

Attest:

MICHAEL K. KIRK

*Attesting Officer*     *Acting Commissioner of Patents and Trademarks*